United States Patent [19]
Bell et al.

[11] 4,157,349
[45] Jun. 5, 1979

[54] DEHYDROHALOGENATION PROCESS

[75] Inventors: Malcolm R. Bell, East Greenbush; John L. Herrmann, Jr., Kinderhook; Vahan Akullian, Menands, all of N.Y.

[73] Assignee: Sterling Drug Inc., New York, N.Y.

[21] Appl. No.: 885,776

[22] Filed: Mar. 13, 1978

[51] Int. Cl.$^2$ ............................................. C07C 45/00
[52] U.S. Cl. ................................................ 260/586 F
[58] Field of Search .................... 260/586 F, 677 X A

[56] References Cited

U.S. PATENT DOCUMENTS

| | | | |
|---|---|---|---|
| 3,920,748 | 11/1975 | Valenta | 260/586 F |
| 3,920,749 | 11/1975 | Cohen | 260/586 F |

OTHER PUBLICATIONS

Ruppert et al., Ber. 106, pp. 3636–3644 (1973).

*Primary Examiner*—Howard T. Mars
*Attorney, Agent, or Firm*—Thomas L. Johnson; B. Woodrow Wyatt

[57] ABSTRACT

5-Ethenyl-4,4a,7,8-tetrahydro-4a-methyl-2(3H)-naphthalenone, an intermediate useful in the total synthesis of steroids, is prepared by dehydrohalogenation of 5-(2-bromoethylidene)-2(3H)-4a-methyl-4,4a,5,6,7,8-hexahydronaphthalen-2-one by a pyrolytic procedure or by means of dehydrohalogenating agents, for example, a mixture of lithium bromide and lithium carbonate.

7 Claims, No Drawings

DEHYDROHALOGENATION PROCESS

BACKGROUND OF THE INVENTION (1) Field of the Invention

This invention relates to a process for preparing a bicyclic trienone, useful as an intermediate for the total synthesis of steroids and analogs thereof, by dehydrobrominating a brominated bicyclic dienone.

(2) Description of the Prior Art

5-Ethenyl-4,4a,7,8-tetrahydro-4a-methyl-2(3H)-naphthalenone, having the structure:

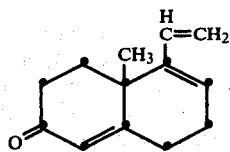

is described by Ruppert et al., Chem. Ber. 106, 3636–44 (1973), as a byproduct obtained in the condensation of the bromoethylidene compound of the formula:

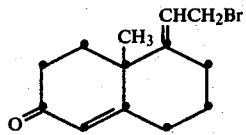

with the sodium salt of 2-methyl-1,3-cyclopentanedione. The main products of the reaction were alkylation products of the cyclopentanedione. The bromide of formula II was in turn prepared by reaction of 5-ethenyl-4,4a,5,6,7,8-hexahydro-5-hydroxy-4a-methyl-2(3H)-naphthalenone of the formula:

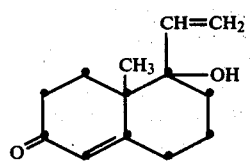

with phosphorus tribromide in methylene dichloride solution.

Valenta U.S. Pat. No. 3,920,748, issued Nov. 18, 1975, describes a process for the total synthesis of steroids in which the initial step is a Diels-Alder reaction between a 2,6-di-lower-alkylbenzoquinone and a substituted 1-vinylnaphthalene compound. One of the suggested intermediate 1-vinylnaphthalene compounds is the structure given in column 13 of the Valenta patent, labeled IIIb and having the structure:

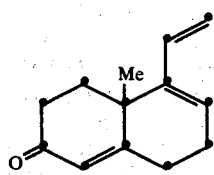

which is the same as formula I given above. The patent states that the structure IIIb can be prepared by dehydration of the vinyl alcohol of structure XXXI, e.g.

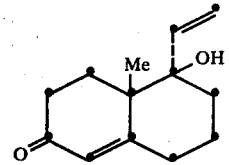

by treating the latter with freshly fused potassium bisulfate and pyrogallol at 145° C. at reduced pressure, although no specific example of this conversion is given. The last paragraph of Example 12 of the patent gives the experimental details of a dehydration of the corresponding vinyl alcohol lacking the endocyclic double bond.

Cohen U.S. Pat. No. 3,920,749, issued Nov. 18, 1975, describes a process for the dehydration of 1β-hydroxy-9β-methyl-1-vinyl-polyhydronaphthalen-6-ones using a Lewis acid such as boron trifluoride etherate to produce a 9β-methyl-1-vinyl-polyhydronaphthalen-6-one with a double bond in the 1,2-position of the naphthalene ring. Example 1 of the patent gives the experimental details of the dehydration of 1β-hydroxy-9β-methyl-1-vinyl-perhydronaphthalen-6-one of the formula:

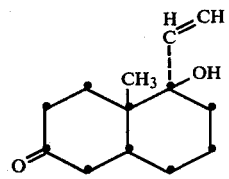

to give 9β-methyl-1-vinyl-3,4,5,6,7,8,9,10-octahydronaphthalen-6-one of the formula:

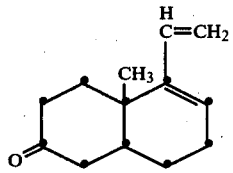

Dehydrohalogenation is a process wherein the elements of halogen and hydrogen are removed from an organic molecule to form a carbon-carbon double bond. A wide variety of reagents have been used to effect this transformation. Lithium chloride or bromide, lithium carbonate or a combination of lithium carbonate and lithium bromide have been used for dehydrobromination of steroid alpha-bromo ketones; cf. Fieser and Fieser, Reagents for Organic Synthesis (John Wiley & Sons, Inc. 1967), Vol. 1, pp. 604–609. Pyridine has been used as a dehydrohalogenating agent, for example in the conversion of 2-(α-chloroethyl)thiophene to 2-vinylthiophene; Emerson et al., Org. Syn. Coll., Vol. 4, 980 (1963).

SUMMARY OF THE INVENTION

This invention relates to a process for preparing 5-ethenyl-4,4a,7,8-tetrahydro-4a-methyl-2(3H)-naphthalenone (Compound I) (formula I above) which comprises heating 5-(2-bromoethylidene)-4,4a,5,6,7,8-hexahydro-4a-methyl-2(3H)-naphthalenone (formula II above) in an inert solvent at a temperature between 75° and 150° C.; or which comprises treating the compound of formula II in an inert solvent with at least one dehydrohalogenating agent selected from the group consisting of pyridine, a lower-alkylated pyridine, an alkali metal phenoxide, a lower-alkylated alkali metal phenoxide, lithium chloride, lithium bromide and lithium carbonate.

DETAILED DESCRIPTION INCLUSIVE OF PREFERRED EMBODIMENTS

When the process is carried out by pyrolysis in the absence of a dehydrohalogenating agent, the nature of the inert solvent is not critical. Illustrative of solvents which can be employed are dimethylformamide, aromatic hydrocarbons such as xylene, toluene and diphenyl; and aromatic ethers such as diphenyl ether.

When the process is carried out in the presence of a dehydrohalogenating agent, a preferred agent is a mixture of lithium bromide and lithium carbonate, and a preferred solvent is dimethylformamide. The process takes place at a temperature between about 50° C. and 150° C. In the mixture of lithium bromide and lithium carbonate, the proportion by weight of $LiBr:Li_2CO_3$ preferably varies between 2:1 and 1:2.

In an especially preferred aspect of the invention, the 5-(2-bromoethylidene)-4,4a,5,6,7,8-hexahydro-4a-methyl-2(3H)-naphthalenone (II) is prepared in situ by reacting 5-ethenyl-4,4a,5,6,7,8-hexahydro-5-hydroxy-4a-methyl-2(3H)-naphthalenone (formula III above) with phosphorus tribromide. In this way, compound I can be prepared from compound III in a single reaction vessel without isolation of intermediate II. Optimum results are obtained by using dimethylformamide as a solvent and a molar ratio of Compound $III:LiBr:Li_2CO_3 = 1:2:3$.

The structure of compound I was proved by elementary analysis and by spectral determinations, e.g. infrared (IR), nuclear magnetic resonance (NMR) and mass spectra (MS). The percent by weight of compound I in any given sample was determined by thin layer chromatography, gas chromatography and NMR measurements.

Attempts to prepare compound I by the procedures suggested in the prior art failed. The procedure of Valenta U.S. Pat. No. 3,920,748, column 18, lines 48–54, was repeated, substituting compound III for the starting material in the patent; thin layer chromatography of the product showed only a trace (less than one percent) of compound I. The procedure of Cohen U.S. Pat. No. 3,920,749, Example 1, column 3, lines 37–49, was also repeated, substituting compound III for the starting material in the patent; there was no detectable amount of compound I in the product upon thin layer chromatography.

The following examples will further illustrate the invention. Although some of the examples do not provide products which are pure compound I, the products are sufficiently enriched in compound I to take part in Diels-Alder reactions with dienophiles such as benzoquinone or derivatives thereof.

EXAMPLE 1

To a solution of 9.0 g. of 5-(2-bromoethylidene)-2(3H)-4a-methyl-4,4a,5,6,7,8-hexahydronaphthalen-2-one (II) in 600 ml. of methylene dichloride was added 500 ml. of xylene, and the mixture was distilled at 55°–60° C. until substantially all of the methylene dichloride had distilled off. The remaining xylene solution was heated in a nitrogen atmosphere at 127°–140° C. for about sixteen hours. The reaction mixture was filtered and the filtrate concentrated in vacuo to yield a residue of 6.6 g. of amber oil. The latter was distilled under high vacuum to yield two fractions, 4.00 g., b.p. 80°–85° C. (0.075 mm) ($n_D^{25} = 1.5631$) and 0.84 g., b.p. 85°–91° C. (0.075 mm) ($n_D^{25} = 1.5642$). The fractions were submitted for mass spectrum (MS), nuclear magnetic resonance (NMR) and ultraviolet (UV) spectral determinations which showed the fractions to be of essentially identical composition, comprising about 77.5% of 5-ethenyl-2(3H)-4a-methyl-4,4a,7,8-tetrahydronaphthalen-2-one (I) and the remainder largely a tricyclic aromatic compound.

EXAMPLE 2

A solution of 0.5 ml. of phosphorus tribromide in 10 ml. of methylene dichloride was added dropwise to a stirred solution of 1.95 g. of 5-ethenyl-4,4a,5,6,7,8-hexahydro-5-hydroxy-4a-methyl-2(3H)-naphthalenone (III) in 25 ml. of dry tetrahydrofuran cooled in an ice-methanol bath. The reaction mixture was then stirred for 2.5 hours at −5°–0° C. and heated on a steam bath for 3 hours. The mixture was cooled and poured into a mixture of 7 ml. of 2 N hydrochloric acid, 20 ml. of water and 50 ml. of ether. The organic layer was separated and the aqueous layer further extracted with ether. The combined ether layers were dried over anhydrous magnesium sulfate and filtered through a pad of sodium sulfate. The filtrate was concentrated at reduced pressure to afford 1.88 g. of oil which was dissolved in ether containing some methylene dichloride, and the solution washed four times with 100 ml. of water and dried over anhydrous magnesium sulfate. The solution was filtered and concentrated to give 0.88 g. (39%) of 5-ethenyl-2(3H)-4a-methyl-4,4a,7,8-tetrahydronaphthalen-2-one (I) containing 20% by weight of the intermediate bromide (II).

EXAMPLE 3

Phosphorus tribromide (0.5 ml., 0.0052 m) in 10 ml. of methylene dichloride was added dropwise to a solution of 1.98 g. (0.0095 m) of 5-ethenyl-4,4a,5,6,7,8-hexahydro-5-hydroxy-4a-methyl-2(3H)-naphthalenone (III) in 25 ml. of dimethylformamide held at −10° to −15° C. After the addition was complete the reaction was stirred for 2.5 hours at −3° to +5° C. At this time 1.5 g. (0.0172 m) of anhydrous lithium bromide and 2.0 g. (0.027 m) of lithium carbonate were added, and the reaction mixture was heated on a steam bath for 3.5 hours. The reaction mixture was poured into a mixture of ice, 2 N hydrochloric acid and ether and shaken. The ether layer was separated, washed with water, dried over anhydrous magnesium sulfate and concentrated to remove the solvent. There was obtained 1.68 g. (94%) of 5-ethenyl-2(3H)-4a-methyl-4,4a,7,8-tetrahydronaphthalen-2-one (I) of 99% purity as determined by NMR spectra.

EXAMPLE 4

A solution of 103.0 g. of 5-ethenyl-4,4a,5,6,7,8-hexahydro-5-hydroxy-4a-methyl-2(3H)-naphthalenone (III) in 1630 ml. of dimethylformamide was cooled to −5° C. in an ice-methanol bath. The solution was stirred while a solution of 25.8 ml. of phosphorus tribromide in 270 ml. of methylene dichloride was added dropwise. The resulting mixture was stirred for 2.5 hours at −5° C. and then there was added in portions a mixture of 75.0 g. of lithium bromide and 105.0 g. of lithium carbonate. The mixture was stirred for 30 minutes at room temperature and then heated on a steam bath for 3 hours. After cooling the mixture it was gradually poured onto a mixture of 1100 ml. of ice-water and 2200 ml. of 2 N hydrochloric acid. The crude product was extracted with ether (six 500 ml. portions) and the combined extracts were washed with water (six 1000 ml. portions) and dried over anhydrous sodium sulfate. The solution was filtered and the filtrate concentrated in vacuo to give 80.6 g. (86%) of 5-ethenyl-2(3H)-4a-methyl-4,4a,7,8-tetrahydronaphthalen-2-one (I) as an oil which upon cooling crystallized to a solid, yellow crystals, m.p. 47°–51° C. The compound is readily recrystallized from aqueous methanol.

| Anal. Calcd. for $C_{13}H_{16}O$: | C, 82.94; | H, 8.57. |
|---|---|---|
| Found: | C, 82.88; | H, 8.71. |
| | 82.85 | 8.79 |

EXAMPLE 5

A mixture of 2 g. of 5-(2-bromoethylidene)-2(3H)-4a-methyl-4,4a,5,6,7,8-hexahydronaphthalen-2-one (II), 1.5 g. of lithium bromide, 2.0 g. of lithium carbonate, 10 ml. of methylene dichloride and 25 ml. of dimethylformamide was heated on a steam bath for 3 hours. The reaction mixture was worked up as described in Example 3 to give 1.22 g. (82%) of 5-ethenyl-2(3H)-4a-methyl-4,4a,7,8-tetrahydronaphthalen-2-one (I).

EXAMPLE 6

A solution of 0.5 ml. (0.0052 m) of phosphorus tribromide in 10 ml. of methylene dichloride was added dropwise to a solution of 1.97 g. (0.0095 m) of 5-ethenyl-4,4a,5,6,7,8-hexahydro-5-hydroxy-4a-methyl-2(3H)-naphthalenone (III) in 25 ml. of dimethylformamide held at 0° to −5° C. addition was complete the mixture was stirred for 2.5 hours at 0°–5° C. Lithium bromide (1.5 g., 0.0172 m) was theded and the reaction mixture heated on a steam bath for 3 hours. The reaction mixture was cooled and poured into a mixture of dilute aqueous hydrochloric acid and ether. The organic layer was separated, dried over anhydrous magnesium sulfate and concentrated to give 1.39 g. of a golden oil containing about 67% of 5-ethenyl-2(3H)-4a-methyl-4,4a,7,8-tetrahydronaphthalen-2-one (I) and 2–5% of intermediate bromide (II) as determined by NMR spectra.

EXAMPLE 7

The experiment of Example 6 was repeated except that the 1.5 g. of lithium bromide was replaced by 2.0 g. (0.027 m) of lithium carbonate. A pale yellow oil (1.40 g.) was obtained which contained about 67% of 5-ethenyl-2(3H)-4a-mehyl-4,4a,7,8-tetrahydronaphthalen-2-one (I) and about 14% of 5-(2-bromoethylidene)-2(3H)-4a-methyl-4,4a,5,6,7,8-hexahydronaphthalen-2-one (II), as determined by NMR spectra.

EXAMPLE 8

The experiment of Example 6 was repeated except that the 1.5 g. of lithium bromide was replaced by a mixture of 1.35 g. (0.0155 m) of lithium bromide and 1.154 g. (0.0156 m) of lithium carbonate. There was obtained 1.37 g. (76.7% yield) of pale yellow oil comprising 5-ethenyl-2(3H)-4a-methyl-4,4a,7,8-tetrahydronaphthalen-2-one (I) of about 95% purity, 2–5% of the intermediate bromide (II) being present, as determined by NMR spectra.

EXAMPLE 9

A solution of 5.94 g. (0.045 m) of potassium phenoxide in 125 ml. of dimethylformamide was added to a solution of 11.7 g. (0.0435 m) of 5-(2-bromoethylidene)-2(3H)-4,4a,5,6,7,8-hexahydronaphthalen-2-one (II) in 75 ml. of dimethylformamide. The reaction mixture was concentrated in vacuo and the residue triturated with xylene and with ether to remove solids. The product was distilled twice under high vacuum, the second distillation at 125°–147° C. (0.09 mm) to give a 17of a liquid product which thin layer chromatography and NMR spectra showed to comprise 5-ethenyl-2(3H)-4a-methyl-4,4a,7,8-tetrahydronaphthalen-2-one (I) as the major component.

It is contemplated that the potassium phenoxide in the foregoing example can be substituted by potassium 4-methylphenoxide, sodium 2,4-dimethylphenoxide or sodium 4-ethylphenoxide with similar results.

EXAMPLE 10

A solution of 0.5 ml. (0.0052 m) of phosphorus tribromide and 0.5 ml. (0.0062 m) of pyridine in 10 ml. of methylene dichloride was added dropwise over a five minute period to a solution of 1.97 g. (0.0095 m) of 5-ethenyl-4,4a,5,6,7,8-hexahydro-5-hydroxy-4a-methyl-2(3H)-naphthalenone (III) in 25 ml. of dimethylformamide held at −20 ° C. The reaction mixture was stirred for two hours at −20°–0° C. and then warmed to room temperature and stirred for 18 hours. The reaction mixture was poured into water and extracted with 150 ml. ether. The ether extracts were washed with 150 ml. of 2 N hydrochloric acid, dried over anhydrous magnesium sulfate and concentrated. There was obtained 1.7 g. of an oil which by NMR spectra was shown to contain about 1.1 g. of 5-ethenyl-2(3 H)-4a-methyl-4,4a,7,8-tetrahydronaphthalen-2-one (I) and about 0.6 g. of 5-(2-bromoethylidene)-2(3H)-4,4a,5,6,7,8-hexahydronaphthalen-2-one (II).

It is contemplated that the pyridine in the foregoing example can be replaced by 4-methylpyridine, 2,6-dimethylpyridine, 2,4,6-trimethylpyridine or 4-ethyl-2-methylpyridine with similar results.

We claim:

1. A process for preparing 5-ethenyl-2(3H)-4a-methyl-4,4a,7,8-tetrahydronaphthalen-2-one which comprises heating 5-(2-bromoethylidene)-2(3H)-4a-methyl-4,4a,5,6,7,8-hexahydronaphthalen-2-one in an inert solvent at a temperatu re between 75° and 150° C.

2. A process for preparing 5-ethenyl-2(3H)-4a-methyl-4,4a,7,8-tetrahydronaphthalen-2-one which comprises treating 5-(2-bromoethylidene)-2(3H)-4a-methyl-4,4a,5,6,7,8-hexahydronaphthalen-2-one in an inert solvent with at least one dehydrohalogenating agent selected from the group consisting of pyridine, a lower-alkylated pyridine, an alkali metal phenoxide, a lower-alkylated alkali metal phenoxide, lithium chloride, lithium bromide and lithium carbonate.

3. A process according to claim 2 in which the dehydrohalogenating agent is a mixture of lithium bromide and lithium carbonate.

4. A process according to claim 3 in which the inert solvent is dimethylformamide.

5. A process according to claim 2 in which the 5-(2-bromoethylidene)-2(3H)-4a-methyl-4,4a,5,6,7,8-hexahydronaphthalen-2-one is prepared in situ by reacting 5-ethenyl-4,4a,5,6,7,8-hexahydronaphthalen-2-one with phosphorus tribromide.

6. A process according to claim 5 in which the dehydrohalogenating agent is a mixture of lithium bromide and lithium carbonate.

7. A process according to claim 6 in which the inert solvent is dimethylformamide.

* * * * *

UNITED STATES PATENT AND TRADEMARK OFFICE
CERTIFICATE OF CORRECTION

PATENT NO. : 4,157,349

DATED : June 5, 1979

INVENTOR(S) : Malcolm R. Bell, John L. Herrmann, Jr. and Vahan Akullian

It is certified that error appears in the above-identified patent and that said Letters Patent are hereby corrected as shown below:

Column 5, line 35, before "addition" insert --After the--;

line 37, "theded" should read --then added--.

Column 6, line 7, "17of" should read --17% yield of--.

Signed and Sealed this

Fourth Day of September 1979

[SEAL]

Attest:

LUTRELLE F. PARKER

Attesting Officer     Acting Commissioner of Patents and Trademarks